(12) United States Patent
Spaulding

(10) Patent No.: US 10,198,659 B1
(45) Date of Patent: Feb. 5, 2019

(54) DIAGNOSTICS AND IMAGING

(71) Applicant: Glenn Spaulding, Houston, TX (US)

(72) Inventor: Glenn Spaulding, Houston, TX (US)

( * ) Notice: Subject to any disclaimer, the term of this patent is extended or adjusted under 35 U.S.C. 154(b) by 301 days.

(21) Appl. No.: 15/015,771

(22) Filed: Feb. 4, 2016

(51) Int. Cl.
*G06K 9/52* (2006.01)
*H04N 5/225* (2006.01)
*H04N 5/44* (2011.01)
*H04N 5/232* (2006.01)
*G06K 9/62* (2006.01)

(52) U.S. Cl.
CPC ............ *G06K 9/52* (2013.01); *G06K 9/6215* (2013.01); *H04N 5/2253* (2013.01); *H04N 5/2254* (2013.01); *H04N 5/2256* (2013.01); *H04N 5/23229* (2013.01); *H04N 5/44* (2013.01)

(58) Field of Classification Search
CPC ....................................................... G06K 9/52
See application file for complete search history.

(56) References Cited

U.S. PATENT DOCUMENTS

| 2004/0237822 A1* | 12/2004 | Boland | B01L 3/0268 101/483 |
| 2007/0231458 A1* | 10/2007 | Gale | B01J 19/0046 427/2.11 |
| 2008/0221406 A1* | 9/2008 | Baker | A61B 5/0059 600/306 |
| 2009/0074282 A1* | 3/2009 | Pinard | G06K 9/00127 382/133 |
| 2010/0081902 A1* | 4/2010 | McKenna | A61B 5/0088 600/324 |

* cited by examiner

*Primary Examiner* — James M Pontius

(57) ABSTRACT

Home healthcare and other clinical solutions are embodied in a platform that diagnoses cancer and other disease states. Representing the lowest cost healthcare solution and a means to reduce healthcare cost; The platform combines imaging and diagnostic technologies with conventional inkjet technologies to provide a contextual diagnostic that will replace most clinical laboratories.

9 Claims, 8 Drawing Sheets

DIAGNOSTICS AND IMAGING

CROSS-REFERENCE TO RELATED APPLICATIONS

This application fully incorporates U.S. Application No. 61/425,591 and claims all current and prior rights. This application fully incorporates U.S. Application No. 61/472,193 and claims all current and prior rights. This application fully incorporates U.S. Application No. 61/540,411 and claims all current and prior rights.

STATEMENT REGARDING FEDERALLY SPONSORED RESEARCH OR DEVELOPMENT

Not Applicable.

REFERENCE TO A "MICROFICHE APPENDIX"

Not applicable.

BACKGROUND OF THE INVENTION

1. Field of the Invention

One of the fields of the present invention is sub 6 mm illumination and imaging wherein illumination is an array of light emitters, imaging utilizing an array of sensors, a deconvolution of the sensor data wherein different combinations of light emitters were turned off and on, and the gap between the light emitter array and sensor array being less than 6 mm.

One of the fields of the present invention is cloud computing for digital image analysis for clinical diagnostics. Images are obtained from an automated digital microscope and uploaded into the cloud. Said images are then stitched to form a larger image then processed by clinical diagnostic engines that yield clinical diagnostic information based on the image processed.

One of the fields of the present invention is adaptive microscope slide staining. A microscope slide with sample is scanned utilizing an automated digital microscope as is known in the art. Biological indicators are deposited onto the sample in quantities and compositions based on the image content and constituent/organelle coordinate.

One of the fields of the present invention is 2D piezo movement. Piezo elements are utilized in an array to concurrent move in 2 dimensions along any vector in that dimension.

One of the fields of the present invention is structure instantiation to determine an optimal focal point and increase resolution.

One of the fields of the present invention is a low inertia ultra small digital microscope with automated x, y, and z axes.

One of the fields of the present invention is inkjet diagnostics. A tissue or fluid sample is disposed to a transparent receptacle suitable for imaging the sample, an inkjet cartridge containing a diagnostic indicator is deposited, or a plurality of cartridges with assorted diagnostic indicators, on to the tissue or fluid and an image obtained using digital microscope imaging means.

One of the fields of the present invention is a progressive camera autofocus means. Said camera having a raster scan sensor configuration collects images and yields an autofocus figure of merit during focus axis transition.

2. Description of the Related Art

Antithetical illumination: In the same month that this provisional patent application was filed one of the most successful, respected and innovative companies, Olympus, published a critical summary of microscopy and imaging components: "The Building Blocks of Micro-Optical Systems Integration: A Primer", Photonics Spectra, December 2010, pg. 46-48. Illuminators have evolved over the last 100 years from candles to laser or LED light sources using the Köhler criteria. Imaging evolved into an objective lens and some combination of exit lens imaging; tube, relay, eyepiece, etc. The illumination goal is directed to wavefront control, ray angles that support objective imaging angles, aberration control, lateral color control, a focal point, and high numerical apertures for wavelength limited resolution. Degradation of any of the parameters results in blurring, loss of resolution, distortion, poor color registration, and lower contrast. The imaging objective collects light from the illumination focal point through co-aligned focal points requiring the illumination goals. Received light rays are refractively guided to a required magnification using optics and typically 160 mm-220 mm light paths, and compensatory design techniques for aberration, later color correction, vignetting etc. Random divergent uncontrolled illumination, without any focal point, without an objective for imaging, will result in a blurred image or no sense of an image at all. The present invention utilizes the illumination and imaging detrimental constructs for imaging; imaging that is capable of sub-wavelength limited resolution.

Neurons can be stimulated by light source to yield an electrical response that is propagated to the brain. And, the brain can send an electrical stimulus to a peripheral nerve that results in a neuro-physical change or yields a biochemical construct that is fluorescent. The ability to detect, translate, and stimulate an in vivo neuropathway does not exist, and does not exist in the required 2-dimensions. The present invention provides a 2-dimensional neuropathway to computer interface useful for controlling robotic limbs.

Cloud Computing: Cloud computing can be defined as moving information on to the internet where specific web based solutions are applied to the information yielding a result. Prior to the disclosed invention, images from fully automated digital microscopes of which few exist, were loaded into the computer associated with said automated digital microscope. The images are then processed and stitched, in few cases diagnostic algorithms applied, and stored on the local hard drive.

Adaptive Microscope Slide Staining: Currently microscopes slides are stained by immersing the slide in a stain, followed by rinsing to remove excess stain. This procedure may be repeated several times with different stains. Stains can include chemical stains, fluorescence stains, stains using labeled antibodies, genetic markers, etc, as is know in the art.

2D Piezo Movement: Piezo elements change size along a single predetermined dimension at nanometer and sub-nanometer increments; movement is controlled through the integration of electrical pulse provided by an external semiconductor controller.

Structure Instantiation: The art teaches that an image is derived from the organization of pixels on a camera sensor with combined optics. Frequency, edge, and other mathematical constructs know in the art assign a figure of merit (FOM) to the degree of blurring of those image pixels. The FOM is then used with apriori knowledge of the current optical design and previous testing, along with another mathematical construct which includes the focusing dimension (e.g., distance to peak FOM), to calculate the optimal focus point. It is the current practice in the art to obtain several FOM along the focusing path to a peak FOM, then FOM beyond the peak to confirm that the FOM did peak.

Low Inertia Microscope: There is no prior art on low inertia microscopes with automated x, y, and z axes.

Inkjet printing has been used in a variety of applications from food processing to printing pictures. It has been available for many decades, yet it has not been used with a pre- and post-microscope imaging process, with deposition based on the context of said pre- and post-images providing cellular features—so the combination is not obvious. Furthermore, prior art does not use said imaging to identify the cell free areas between cells or tissue deposed to a receptacle for selective utilization of intercellular constituents for diagnostic determinations.

Autofocus technologies have been available for decades. Current cameras incorporate stability and stabilization technologies to compensate for the blurring of movement during image acquisition. In raster scanned cameras, rows are sequentially exposed thus movement during exposure blurs the image. New blur mitigation technologies include global shutters to synchronize image exposure, and software compensation for image stabilization.

SUMMARY OF THE INVENTION

Antithetical illumination: One of the present inventions utilizes an array of light emitters less than 6 mm away from a sensor array. Divergent light from an emitter impinges upon more than one pixel in the sensor array. An object interposed between the illuminator and sensor will modify the illumination as seen by the sensor. Because each emitter directly illuminates more than one pixel, is not focused, and there are no high numerical aperture receiving optics, an image of an object interposed between the illuminator and sensor will be blurred. Moreover, blurring will increase with an increase in the number of pixels illuminated by one emitter. However, one emitter can be turned on and the multi-pixel illumination deconvolved to form a light ray construct for that emitter; and every emitter in the emitter array individually deconvolved. Having the ray construct for each emitter and interposing a tissue between the emitter and sensor, enables sub-wavelength image construction by turning one emitter on collecting pixel data, turning it off then turning on an adjacent emitter collecting pixel data, then applying iterative higher deconvolution/convolution and mathematical techniques that are known in the art to construct the image. Furthermore, with the light path less than 6 mm, the overall volume of the illumination and sensor would be less than 1 cubic centimeter: amenable for implantation. Resulting images are mathematically derived.

Different neurons have peak responses to different wavelengths. Emitters that have wavelengths tailored to specific neural subtype stimulation can be interposed in the array between other emitters. It is anticipated that different wavelength emitters will be used in an array for stimulation and/or imaging.

Cloud Computing: One of the present inventions utilizes cloud computing for stitching images, providing clinical diagnostics from said images, then storing said images; said images obtained from a fully automated digital microscope.

Adaptive Microscope Slide Staining: One of the present inventions utilizes ink jet printing technologies to localize stains to specific regions of a microscope slide. Said region may be as large as the entire sample that is present on the slide, or as small as an organelle or DNA or RNA fragment. Segments of said slide where the sample is not present are not stained—which is not the case for current slide staining procedures.

2D Piezo Movement: The present invention utilizes piezo elements in an array oriented 90 degrees to one another in a checker board pattern.

Structure Instantiation: The present invention instantiates a structure and finds that structure in an image. The differences between the model and image are utilized to build a mathematical construct for focusing and increasing resolution, as well as improving other esthetic image features.

Low Inertia Microscope: The present invention discloses an ultra small, low inertia, digital microscope with automated x, y, and z axes.

Inkjet Diagnostics: The present invention discloses a method to obtain clinical diagnostic information on cells and tissues and the constituents deposed to a receptacle; that combines digital microscope imaging and inkjet printing wherein a first digital microscope image is collected to identify cellular and tissue structures, diagnostic determinants contained within an inkjet cartridge(s) are deposited on to said based on cellular and tissue structure context, a second digital microscope image is collected which includes the selected inkjet cartridge deposition, and the selective deposition is of clinical diagnostic value.

Raster Scan Autofocus: The present invention discloses movement during a raster scan exposure, which the art teaches against, whereby the blurring result is used to determine an autofocus figure of merit.

DETAILED DESCRIPTION OF THE INVENTION

Figure 1:
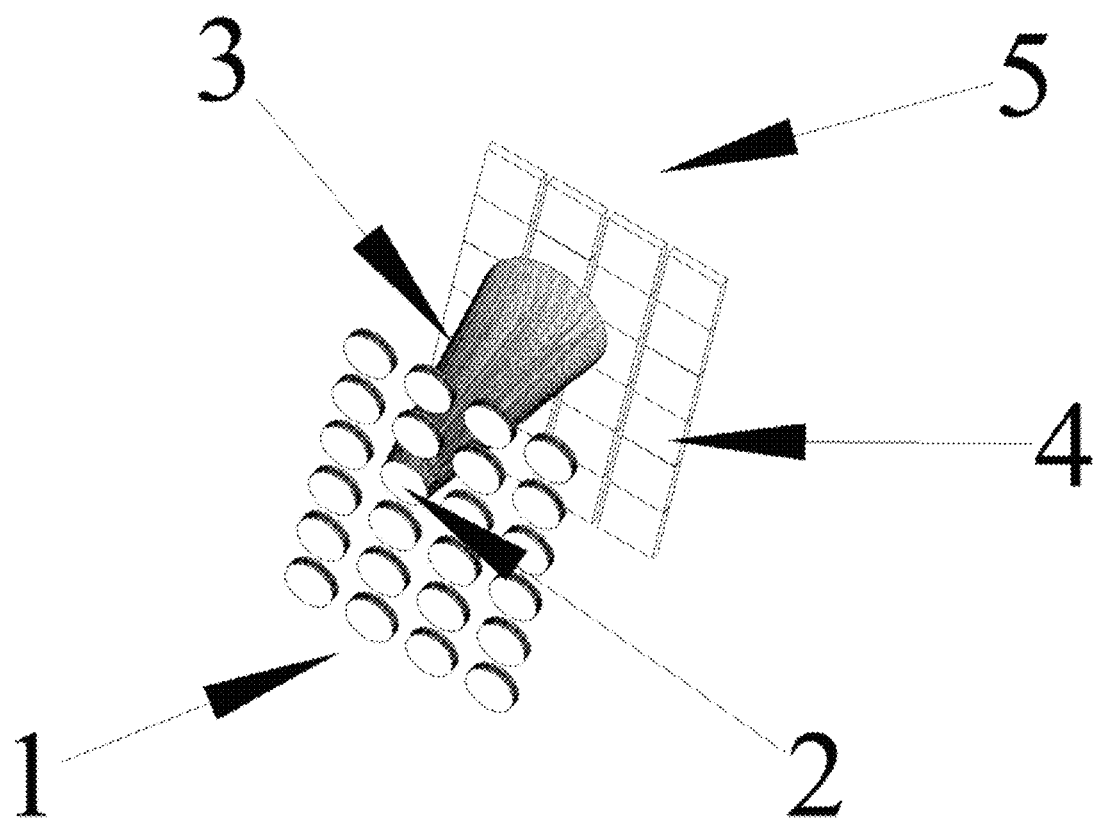
FIG. 1 is a schematic illustration of antithetical illumination and imaging.
Figure 8:
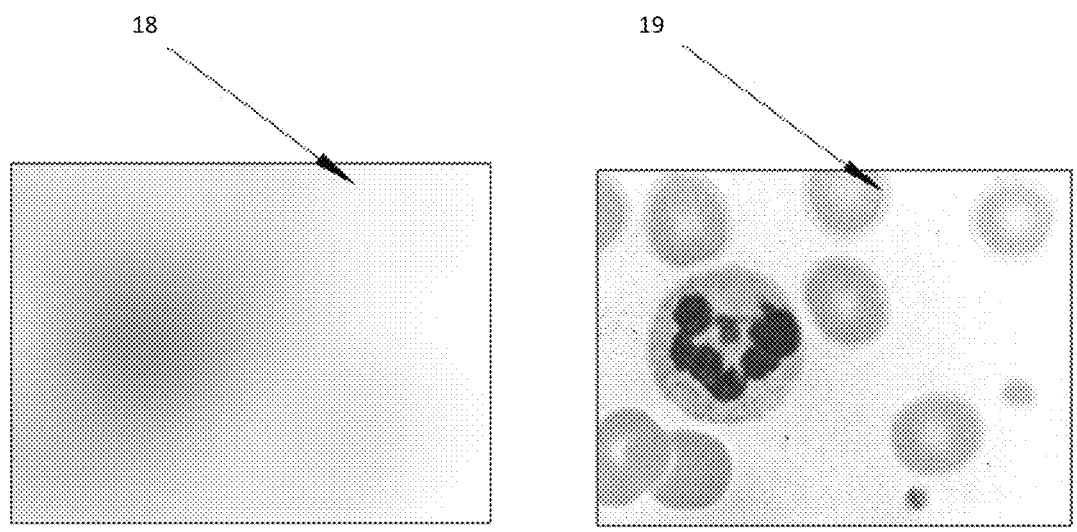
FIG. 8 is an image blur to restructure illustration.

Antithetical Illumination: FIG. 1 is a schematized illustration of an embodiment wherein a light emitting array land a sensor array 5 are separated by a <6 mm gap. Light from an emitter 2 has a diverging cone of light 3 that impinges on pixels 4 in the sensor array 5. Said emitters can consist of lasers, quantum lasers, plasmon lasers, LEDs, OLEDs, and the like that are known in the art; each having a divergent cone angle 3. In FIG. 1 the emitter light 3 illuminates two or more pixels in the sensor array 5. The illumination of multiple pixel enables the deconvolution of the illumination cone 3. Pixels will range in size from below 1 micron to 10 microns, emitters will have a substantially broader size range that depends on the pixel size, type of tissue and image required. In a preferred embodiment emitter elements and sensor pixels are of similar size. Increasing the number of pixels illuminated by one emitter will increase the deconvolution solution and help support interposed wavelengths. In a further embodiment, there is no focal point nor does tissue have to be at the focal plane for imaging. The invention enables the use of juxtapositioned cone angles to be used to determine and accommodate depth—the distance from the sensor. Sensors include CMOS, CCD, photodiodes, and the like. FIG. 8 is an image blur to restructure illustration.

Figure 5:
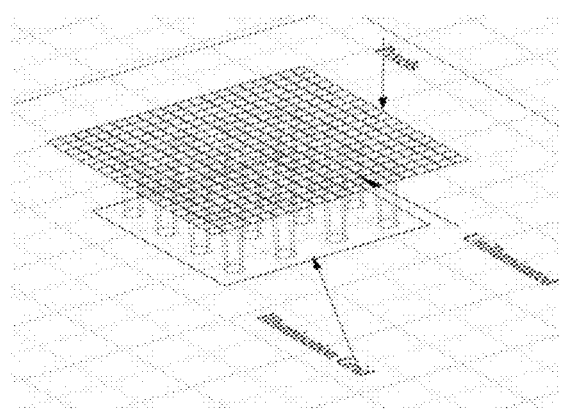
FIG. 5 is a antithetical illumination with shifting illumination grid schematic illustration.

In an extended embodiment, a grid of pin holes is placed over the illumination array (FIG. 5, illumination grid). The grid is arranged such that illumination cones impinge upon the pixel camera but do not overlap yielding un-illuminated pixels (FIG. 5 Un-illuminated). An image is collected from the illuminated pixels and stored. After storing the image, the illumination grid is shifted such that the illumination cones impinge upon the pixel sensor but shifted to an adjacent position. The shift distance is dependent upon the resolution needed in constructing the final image. In general, the cone angle and the shift distance determine the resolution. In this instant invention multiple areas are illuminated without overlap instead of one cone illumination, resulting in quicker image acquisition.

In another embodiment, a neural bundle is routed through the emitter/sensor gap. Prior to routing the neural bundle illumination for each emitter was deconvolved. After implantation and neural bundle routing, an image of the neural bundle is collected during electrical inactivity. The image becomes a baseline to determine changes during activity and to localize areas in the neural bundle that are most active for later stimulation. Quantization of morphological perturbations or fluorescence becomes the determinate for specific motor movement in the artificial joint.

Figure 2:
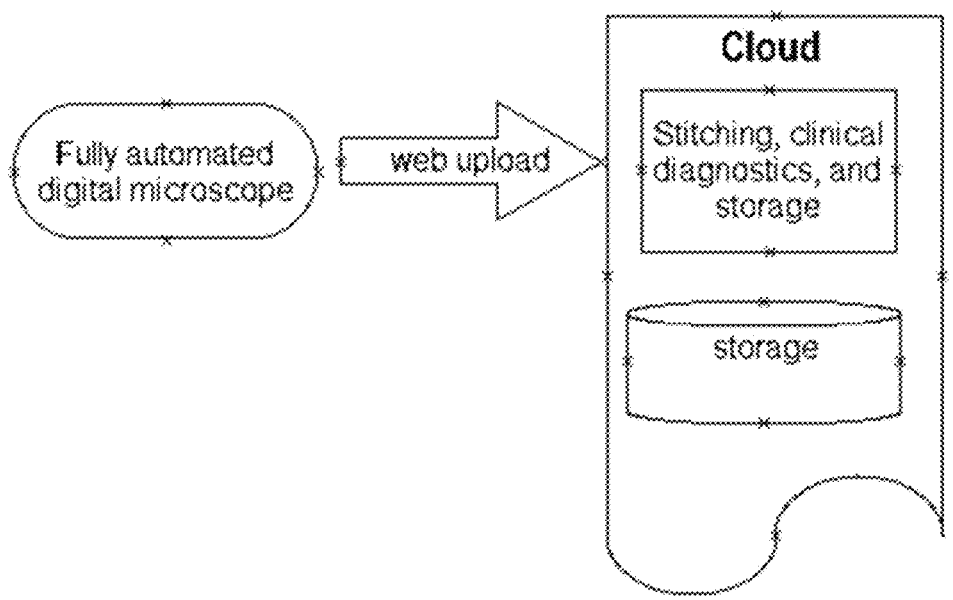
FIG. 2 is a schematic illustration cloud stitching, clinical diagnosis, and storage.

Cloud Computing: FIG. 2 is a schematized illustration of an embodiment wherein a fully automated digital microscope uploads images from scanning a microscope slide to an internet cloud. Said cloud is tailored to accept said images from said microscope slide. Said accepted images are then stitched (or tiled) together to form a larger image. Said larger images are analyzed utilizing software algorithms for diagnostic content then stored. Said diagnostic content can include but is not limited to hematology, cytology, parasitology, cancer, slide constituents, etc., as is known in the art. Said fully automated digital microscope refers to an imaging system whereby 1) the x, y, z motion control is computer driven through motion controllers known in the art such as motors, piezo, magnetic fields, and the like; 2) Said fully automated digital microscope includes 3) a digital camera having greater than 1,000,000 pixels with said pixel area size less than 100 square microns; Said fully automated digital microscope having 4) autofocus utilizing said motion controllers; and said automated digital microscope not having 5) optical elements for directly viewing the sample.

Figure 3:
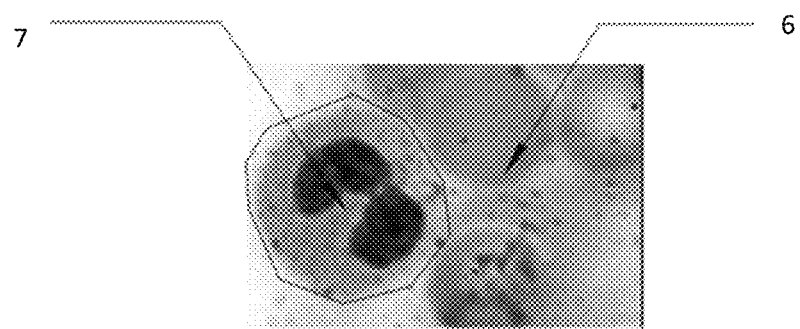
FIG. 3 is a schematic illustration of selective staining based on image content.

Adaptive Microscope Slide Staining: One of the present inventions discloses an adaptive microscope slide staining invention whereby specific regions of a microscope slide are stained with specific stains, specific grouping of stains, or stained with different stains in a specific order (FIG. 3). A slide may be first scanned by an automated digital microscope. The image is then used to identify regions, structures, cell types, anomalies and such known in the art. Since the slide has been imaged, pixel coordinates are implicit within image and are used to move the ink jet printer head to that location. Just as an ink jet printer can deposit different colors, in the present invention different stains are deposited at specific coordinates, mixed or in a specified sequence. Thus the staining sequence or composition, and location is adapted to the underling content. In doing so specific anomalies can be enhanced locally without globally staining other structures—the consequences being the blurring of other constituents through the use of an unnecessary stain in that region. The image may be a high resolution image so to identify specific structures or an overview region to identify tissue location. Alternatively, the slide may be stained prior to scanning.

Adaptive microscope slide staining is further disclosed for other uses which include hematology, cytology, parasitology, cancer, genetic markers, protein markers, RNA markers, DNA markers, slide constituents, etc., as is known in the art. For example, a group of cells may look suspicious for cancer and different cancer fluorescent tags deposited at the coordinates for specific suspicious cells therein used to identify specific subtypes yet eliminating the background artifacts associated with staining the entire slide at one time—increased specificity and sensitivity.

In an alternative embodiment of adaptive microscope slide staining, a whole blood sample is dispersed on a slide for a hematology differential. The slide may be stained as in the previously disclosed invention or not, however in addition to the wells that contain stain for dispensing, other wells are included that have colorimetric, fluorometric, or other indicators known in the art. Said indicators change color, or other properties know in the art, with a specific constituent. For example, a colorimetric indicator for glucose may be use. Said glucose indicator would be applied by the above disclosed invention as a droplet in an open space between two cells. Said glucose would then react to the blood serum constituents present in the underlying portion of the slide where the droplet was applied and yield a color change indicative of the glucose concentration. The ensuing image would provide both the hematology differential (information on whole blood counts) as well as chemical and/or biological constituents contained within the sample. The possible indicators and multiple indicators can be added to a sample, include all the clinical tests current utilized in clinical and research testing. Samples can include but are not limited to, whole blood, serum, sputum, feces, cerebral fluid, tissue, exudates, etc. A slide can be any vehicle the samples are disposed to and on which said samples can be imaged.

Figure 4:
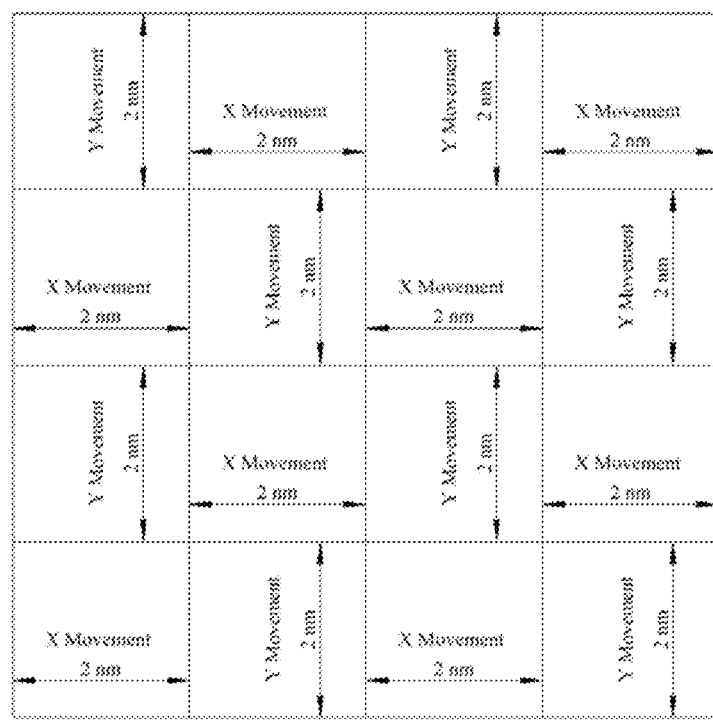
FIG. 4 is a schematic illustration piezo element layout for 2 dimensional movement.

2D Piezo Movement: The invention is disclosed (FIG. 4) whereby two dimensional movement vectors are obtained utilizing piezo elements. In FIG. 4 a 2 nanometer movement vector is illustrated for each piezo element. The checker board pattern enables both contiguous and concurrent movement in two dimensions. In an alternate embodiment, piezo elements are separated from juxtapositioned elements by materials having elasticity, such that as the elements expand or contract, said interspaced material absorbs the movement imparting movement isolation at each piezo element site.

Structure Instantiation: In the present invention an image is collected and one or more models are instantiated. Models may be two dimensional or three dimensional, be simple models or full fidelity e.g., textured, semi-transparent, bifringent, etc as is known in the art. In one illustration, an image structure for example a red blood cell is compared to a red blood cell instantiation model. Said instantiation is then scaled and axial vector aligned using methods known in the art. A point spread function (PSF) is derived from the red blood cell region of the image and applied to said instantiation model to yield an image; the PSF and application is know in the art and available in freeware. The difference between the red blood image and the PSF derived image from said instantiation model, represents the optical, electrical, mechanical, and other noise in the imaging system.

The noise difference can be deconvolved/convolved into an imaging class, for example vignetting, and the vignetting coefficients determined. Said vignetting coefficients are utilized to reprocess the original image thereby removing the vignetting noise. Noise is a component of resolution. By instantiating a model structure and comparing as above the PSF can be sharpened as known in the art, then used to increase resolution to super-resolution—not wavelength limited. Alternatively, reprocessing the image to remove vignetting can be iterative utilizing said instantiating model as an idealized endpoint and thereby constraining the processing time. Once the coefficients for noise have been derived for each class utilizing the idealized instantiation, those coefficients can be used to reprocess the entire image, removing the noise from the entire image. This is especially useful in microscopy where the structures on the microscope slide are known before the slide is loaded into the digital microscope for imaging. Said instantiation models can include but are not limited to, cells, red blood cells and subtypes, white blood cells and subtypes, DNA, RNA, organelles, bacteria, platelets, parasites, chromatin, and other constituents found in tissue and body fluids, as is know in the art. Said sources of imaging noise are know in the art and included herein.

Structure Instantiation: In an alternate invention embodiment, structure instantiation is used to refine the identification of diagnostically useful structures in microscopic analysis of tissue or body fluids. In one illustration, a whole blood sample is imaged on a microscope slide where Auer bodies are suspected to be present. Thresholding, edge detection, watersheding, and other mathematical constructs statistically converge on the identification of the structure within the image. Using the PSF from the image Auer body and applying the PSF to the idealized instantiated model as previously described will yield the deviation from ideal, and therefore a metric for mitigating false positives and negatives. The combination of both instantiation inventions would further improve diagnostic reliability. PSF and other mathematical constructs are know in the art and can be used to determine differences.

Structure Instantiation: In an alternate invention embodiment, structure instantiation is used for autofocusing. In one illustration, a microscope slide with a tissue sample on the slide is inserted into a digital microscope. Said sample includes cells with nuclei and an image is collected. A nuclei structure instantiation is used as previously described to quantify the differences between PSF of idealized instantiation and the image structure. The differences between the two images are directly related to the focus distance and therefore can be used as a figure of merit for focusing as is known in the art.

Low Inertia Microscope: Low inertia is achieved through the combination of plastics to reduce weight and inertia, rigid guide rods to maintain rigidity and alignment, a common frame to mitigate image distortion caused by vibration by linking all axes making the vibration synchronous, and utilizing software to compensate for the inequities between plastic and metal. The z axis is moved independently but is disposed to the x and y axes such that movement of the x or y axes moves the z translational means. Said 3 axes and translational means weight less than 2 kg.

Figure 6:
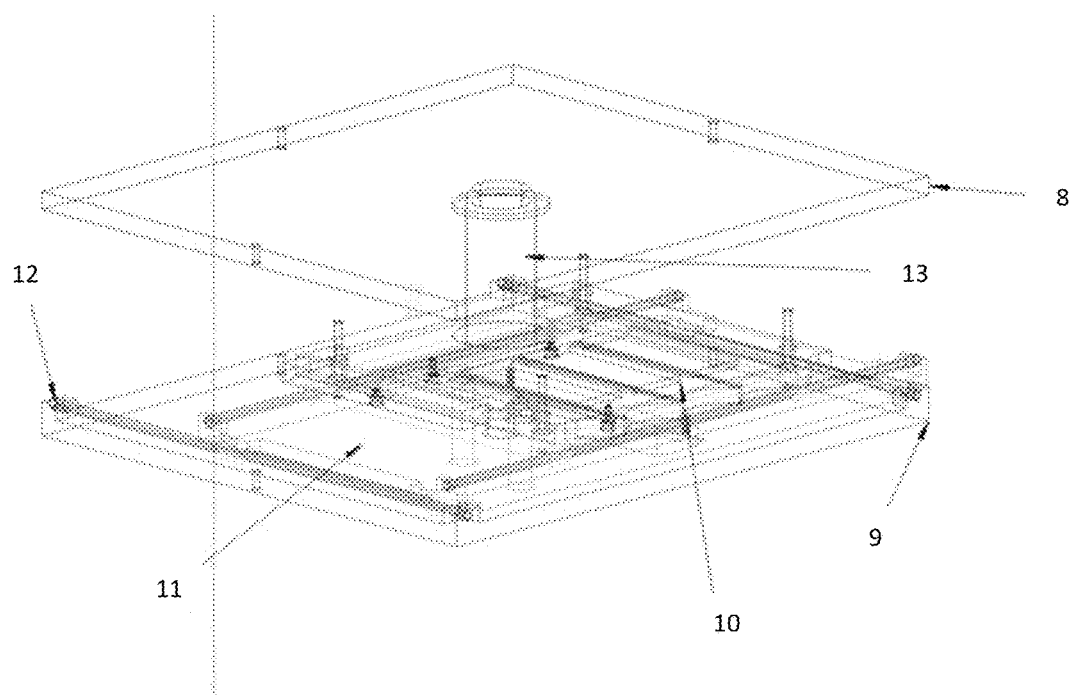
FIG. 6 is a schematic illustration of a low inertia microscope.

FIG. 6 is a schematic illustration of a low inertia microscope. The frame 1 & 2 which are linked together to become one solid unit house the horizontal X 3 and Y 4 axis as well as the imaging optics 6 and illumination source. Rods, 5 illustrates one of the rigid guide rods, supports X 3 and Y 4 axes, and enables Y axes 4 and X axes 3 to slide in one axes resting on the rods. The Z axis is disposed to the top of the X 3 axis. The volume of the microscope housing per slide receivable, in this case 3 slides, is substantially less than prior art approaches. Because of the inherent elasticity of plastics, plastics with fillers, and composite plastics, the elasticity flex leads to unstable imaging and poor coordinate positioning. The rods 5 provide additional rigidity and a low wear low friction surface for the axes to slide upon; with negligible weight/inertia increase. Movement means are deposed to the frame or axes to provide axial movement. Said movement means can be but are not limited to, piezo, stepper motor, DC motors, AC motors, magnetic coils, and the like, also to include gears, belts, synchromeshes, and the like. An imaging device, for example a CMOS camera, is deposed to the frame 1 for stability obtaining the image from the imaging optics 6. For fine movement and imaging resolution, the compensatory means include software solutions known in the art and include but are not limited to, stepper motor controls, image positioning, encoders, predictive motion control, and the like. The movement of the X 3, Y 4, and Z axes by motors under the control of software is herein referred as automated. The camera and software impart digital, thus the microscope herein disclosed is a plastic digital automated microscope. This microscope provides wavelength limited or better resolution.

Figure 7:
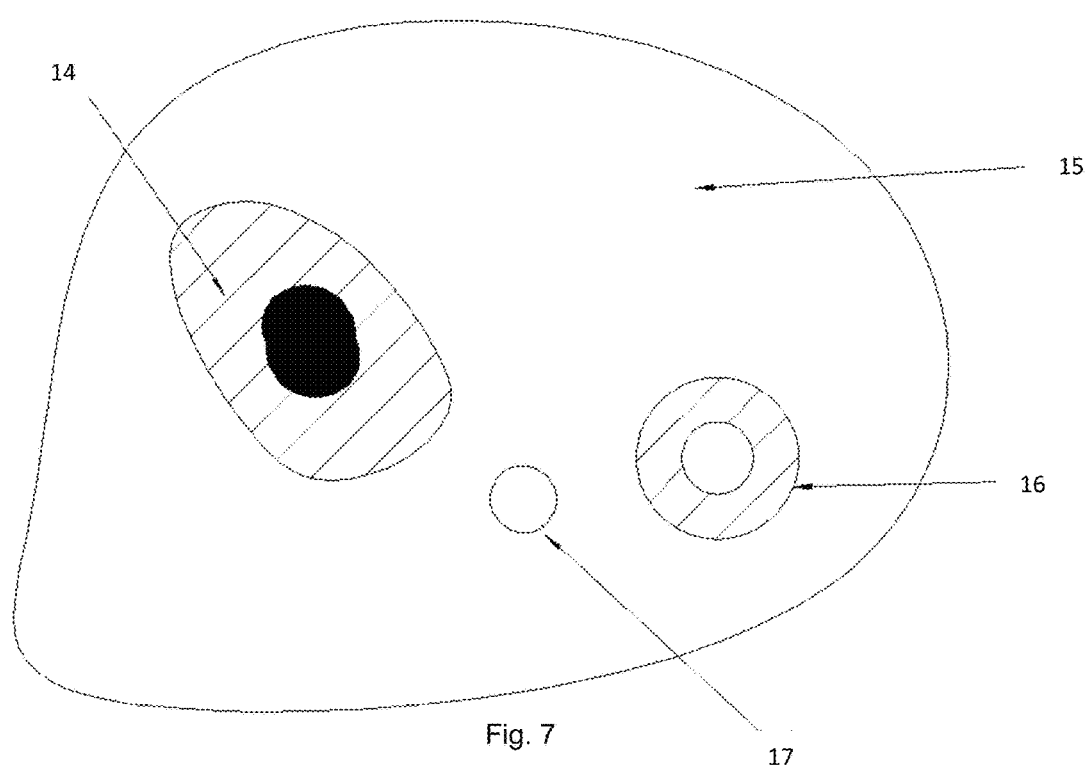
FIG. 7 is a schematic illustration of the results from an inkjet selective deposition method for clinical diagnostics.

FIG. 7 is a schematic illustration of the results from an inkjet selective deposition method for clinical diagnostics. The inkjet selective deposition of diagnostic indicators relies on two digital microscope images; the first image identifies cellular and tissue features and the second image provides a view of the deposited diagnostic indicator. In one hematological embodiment, a whole blood droplet is disposed to a microscope slide as is known in the art, and dried by methods known in the art. FIG. 7 depicts the area of dried whole blood deposition. The deposed dried whole blood sample is imaged, and based on said image an inkjet droplet 4 is deposited between a white blood cell 1 and a red blood cell 3 onto the intercellular constituents 2. A second digital microscope image is collected having a view of the deposited inkjet droplet 4. Said inkjet droplet 4 is a clinical diagnostic indicator. Said indicator reacts to whole blood constituents 2 in a visual manner that can be seen in the second digital microscope image. Said reactions can include but are not limited to colorimetric, enzymatic, fluorometric, polarimetric, wave front shifting or other spectral changes that can be viewed in the second image. Indicators can include but are not limited to stains, enzymes, antibodies, aptamers, RNA, DNA, PCR, dyes, gold beads, nano-indicators, and others that have sensitivities to whole blood constituents that are known in the art 2. Multiple diagnostic indicator droplets can be deposited on the same whole blood sample, each indicator having a different diagnostic value. Different indicators and reactions can be utilized in different combinations in different droplets. The disclosed invention can use sources other than whole blood that are deposed to a receptacle by means know in the art including but are not limited to sputum, swabs for throat culture, spinal fluid, cerebral fluid, urine, cervical swabs, feces, biopsy, and other clinical specimens. The imaging resolution shall be sufficient to resolve cellular edges, and better than 2 micron resolution is preferred. Movement resolution must support imaging and positioning correspondence that enables inkjet droplet deposition on an image selected cell.

In an embodiment for home healthcare, inkjet diagnostics of the present invention are combined with the low inertia microscope present invention to provide a healthcare platform herein disclosed as a new invention. Said healthcare platform is comprised of a low inertia microscope that can receive a receptacle having a sample for diagnostic evaluation e.g., whole blood. Said low inertia microscope having digital image collection means and inkjet droplet dispensing means, and collects an image then dispenses a diagnostic droplet onto the receptacle using inkjet droplet dispensing means and the cellular context from said first image. Said platform collects said second image having a view of the cellular components of the source and a view of the diagnostic droplet. Said second image is provided to an algorithm for diagnostic information. Said diagnostic information does not require a physician for interpretation or confirmation. Said algorithms are know in the art and include but are not limited to hematology algorithms for determining cell type, colorimetric algorithms for color density, urinary algorithms for identifying urinary cellular/bacteria/protein structures, algorithms for parasite identification, and the like known in the art. Said algorithms can reside on a locally housed computer or the cloud of the present invention.

In an embodiment for raster scan autofocusing means, a raster scanned image sensor is used to collect an image during an autofocus axis translation which yields an autofocus figure of merit (FOM). In an illustrative embodiment, a raster scanned CMOS camera sensor is used to collect images. After exposure begins for the second image, the object or camera begins movement towards the focusing point along the focusing axis; the movement can but is not required to move past the focusing point. Said movement occurs during the exposure period of the second image. Consequently, each row of pixels shifted out during the movement will contain image information at sequential points along the movement axis—yielding blur in the overall image. However, the exposure delta between adjacent pixels on the same row is negligible. Thus, an FOM of each row is a valid indicator for optimizing focal position. Said FOM can use but is not limited to a sum-of-the-difference between adjacent pixels in the same row; yielding an FOM for each row. As the focusing axis moves towards the point of optimal focus, the FOM increases and peaks at optimal focus (decreasing as it moves past the focus). The instant invention results in an FOM that can be used to determine optimal focal position. In a further embodiment, said FOM is instantiated in an algorithm that predicts the point along the focus axis where focus will be optimal. Said algorithms are known in the art and include, but is not limited to polynomial functions. In a 1080p sensor, as few as three rows are needed for determining the optimal focus position. In an image with few structures and substantial open space, a first image is collected prior to movement, and a second image collected during movement. The first image is used as a reference to compensate for open spaces in the image as is known in the art.

It is clear that the afore mentioned inventions and embodiments are a departure from convention. It will be recognized by those skilled in the art that changes may be made to the above-described embodiments of the invention without departing from the broad inventive concepts thereof. It is understood therefore, that this invention is not limited to the particular embodiment disclosed, but is intended to cover any modifications that are within the scope and sprite of the invention as defined by the appended claims.

The invention claimed is:
1. An illumination and imaging system comprised of:
a two-dimensional light emitting array,
said emitting array emitting divergent light toward a sensor,
said sensor having sensing elements in a two-dimensional array,
the distance between said emitting array and said sensor array is less than 6 mm, and
said emitting array and said sensor array form an illumination and imaging system for cellular imaging wherein said system has a spatial resolution that resolves cells and their intracellular constituents.

2. The illumination and imaging system of claim 1 wherein a neural bundle is interposed in the illumination space between said two-dimensional illumination array and said two-dimensional sensor array,
the activity of said neural bundle is detected by said sensor array therein forming an image of the neural bundle activity and placing that image information on the computer interface, and
said illumination array, said sensor array, and said neural bundle form a neural bundle to computer interface.

3. The illumination and imaging system of claim 1:
wherein images, obtained from said sensor array, have sub-wavelength spatial resolution.

4. A clinical diagnostic platform comprising:
a digital microscope having computer controlled x, y, and z axes,
the combination of said microscope and said computer control providing x and y axes positioning and z axis autofocus imaging,
an inkjet cartridge having clinical diagnostic indicators in said inkjet cartridge,
said positioning and imaging control is used to place a droplet from said inkjet cartridge on to a previously identified cell;
said previously identified cell having been previously identified by said positioning and imaging control,
adaptively deposing said droplet on to said cell based on the viewed cellular context provided from said positioning and imaging control, and
viewing said adaptive results using said positioning and imaging control.

5. The clinical diagnostic platform of claim 4 linked to a cloud service for uploading images obtained from a microscope specimen slide comprising:
said clinical diagnostic platform of claim 4,
said platform linked to a cloud service,
said platform having said microscope specimen slide and using said positioning and imaging control to collect images from said microscope specimen slide,
said images uploaded to said a cloud service for stitching, clinical diagnostics, and storage in said cloud, and
said images uploaded to said cloud service having said adaptively deposed indicator information in said images.

6. The clinical diagnostic platform of claim 4:
wherein said positioning and imaging control are derived from an autofocus,
wherein said autofocus uses a raster scanned two-dimensional image sensor,
translation along the autofocus focus axis occurs during the sensor exposure period, and
deriving an autofocus figure-of-merit representing the current focus during said axis translation.

7. The clinical diagnostic platform of claim 4 having two-dimensional vector movement comprised of:
piezo elements arranged in a two-dimensional checker board array,
said array imparting forces along a two-dimensional vector, and
said vector imparting movement.

8. A method for digital microscopy image improvement comprised of:
- obtaining an image of an individual cell from a digital microscope having x and y axes positioning control, and z axis autofocus control,
- identifying a cell structure in said image and instantiating a mathematically similar structure to said identified structure,
- comparing said image structure to said instantiated mathematically similar structure, and
- improving said image, using the differences and the similarities between said instantiated mathematically similar structure and said image structure obtained from said comparison.

9. The image improvement of claim 8 wherein
said image improvement includes sub-wavelength spatial resolution.

\* \* \* \* \*